United States Patent
Hahn et al.

(10) Patent No.: US 6,212,431 B1
(45) Date of Patent: Apr. 3, 2001

(54) POWER TRANSFER CIRCUIT FOR IMPLANTED DEVICES

(75) Inventors: Tae W. Hahn, Northridge; Glen A. Griffith, Newbury Park, both of CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/376,881

(22) Filed: Aug. 18, 1999

Related U.S. Application Data
(60) Provisional application No. 60/099,433, filed on Sep. 8, 1998.

(51) Int. Cl.$^7$ .................................................. A61N 1/378
(52) U.S. Cl. ........................................................... 607/61
(58) Field of Search ................................ 607/61, 32, 33, 607/55, 56, 57

(56) References Cited

U.S. PATENT DOCUMENTS

| | | | |
|---|---|---|---|
| 4,134,408 | 1/1979 | Brownle et al. | 128/419 |
| 4,223,679 | 9/1980 | Schulman et al. | 128/419 |
| 4,654,880 | 3/1987 | Sontag | 455/41 |
| 5,069,210 | * 12/1991 | Jeutter et al. | |
| 5,117,825 | 6/1992 | Grevious | 128/419 |
| 5,314,453 | 5/1994 | Jeutter | 607/61 |
| 5,603,726 | 2/1997 | Schulman | 607/57 |
| 5,674,265 | 10/1997 | Deschamps | 607/60 |
| 5,690,693 | 11/1997 | Wang et al. | 607/61 |
| 5,713,939 | 2/1998 | Nedungadi et al. | 607/33 |
| 5,715,837 | 2/1998 | Chen | 128/899 |
| 5,876,425 | 3/1999 | Gord et al. | 607/56 |

* cited by examiner

*Primary Examiner*—Scott M. Getzow
(74) *Attorney, Agent, or Firm*—Bryant R. Gold

(57) ABSTRACT

An external power transfer circuit (12) couples ac power having a fixed frequency into an implantable electrical circuit (14), e.g., an implantable tissue stimulator, while automatically maintaining optimum power transfer conditions. Optimum power transfer conditions exist when there is an impedance match between the external and implanted circuits. The external transfer circuit includes a directional coupler (42) and an impedance matching circuit (44). The directional coupler senses the forward power being transferred to the implant device, as well as the reverse power being reflected form the implant device (as a result of an impedance mismatch). The impedance matching circuit includes at least one variable element controlled by a control signal. The sensed reverse power is used as a feedback signal to automatically adjust the variable element in the impedance matching circuit, and hence the output impedance of the external power transfer circuit, so that it matches the input impedance of the implant device, despite variations that occur in the input impedance of the implant device due to variations in implant distance and implant load.

15 Claims, 3 Drawing Sheets

POWER TRANSFER CIRCUIT FOR IMPLANTED DEVICES

This application claims the benefit of U.S. Provisional Patent Application Serial No. 60/099,433, filed Sep. 8, 1998, which application is incorporated herein by reference..

BACKGROUND OF THE INVENTION

The present invention relates to an implantable electrical device, e.g., an implantable medical device such as an implantable cochlear stimulation system, which receives its operating power and/or which receives recharging power from an external (non-implanted) power source.

Implantable electrical devices are used for many purposes. A common type of implantable device is a tissue stimulator. A tissue stimulator includes one or more electrodes in contact with desired tissue. An electrical stimulation current is generated by the stimulator and applied to the tissue through the electrode(s).

In order for an implanted device to perform its intended function, e.g., to generate an electrical stimulation current, it needs a power source. Some implanted devices, e.g., cardiac pacemakers, employ a high capacity battery that has sufficient power stored therein to provide operating power for the device for several years. Other implanted devices, e.g., a cochlear stimulation system, do not use an implanted power source bur rather receive a continuous stream of power from an external source through an rf or inductive link. Yet other implanted devices include a rechargeable power source, e.g., a rechargeable battery, that must be regularly recharged, e..g, once a day, or 2–3 times per week, from an external source in order for the implanted device to operate. The present invention is intended for use with the latter two types of implanted devices, e.g., those that receive a continuous stream of operating power from an external source, or those that must receive power at regular intervals in order to recharge an implantable power source.

Power is typically coupled to an implanted device through inductive coupling. That is, an external coil receives an ac power signal. An implanted coil connected to, or forming part of, the implantable device, is placed in close proximity to the external coil so that magnetic flux generated by the ac power signal in the external coil induces an ac power signal in the second coil, much like the primary winding of a transformer couples energy to a secondary winding of the transformer, even though the two windings are not electrically connected to each other. When coupling power to an implanted device in this manner, an optimum power transfer condition exists only when there is a good impedance match between the implant device and the external device. While impedance matching schemes can and have been used in the external device, such matching schemes are only effective for a given distance between the external coil and the implant coil, and for a given load attached to the implant device.

Unfortunately, neither the load associated with the implant device nor the separation distance between the external coil and the implant coil are constants. Each of these parameters are, in practice, variables, that may vary, e.g., from 3-to-15 mm for the separation distance, and 20 to 300 ohms for the load. As a result, optimum power transfer between the external device and implant device is rarely achieved. Thus, a less than optimum power transfer condition exists and much of the energy sent to the external coil is lost. What is needed, therefore, is a way to assure that optimum power transfer conditions exist between the external coil and implant device at the time a power transfer is made.

For many implant devices, optimum power transfer has heretofore generally not been a serious concern inasmuch as the external device (which has generally comprised a relatively large device that is worn or carried by the patient) has been viewed as having a potentially infinite power source (through recharging and/or replacing its battery). Unfortunately, however, transferring large amounts of power without concern for how much power is lost is not only inefficient, but may create regulatory problems. That is, most regulatory agencies stipulate the power levels that may be used with an implant device.

Further, new generation external devices are being made smaller and smaller to accommodate the needs and desires of the user. For example, a behind-the-ear (BTE) external device may be used with an implantable cochlear stimulator (ICS). Such BTE external device that is about the same size as a conventional behind-the-ear hearing aid. Such smaller devices, as a practical manner, do not have a potentially infinite power source, but must be powered using a small button battery, or equivalent. Such small battery must provide power for both the external unit and the implant unit, and achieving an efficient power transfer is a key element in assuring a long battery life.

It is known in the art, see, e.g., U.S. Pat. No. 4,654,880, to include the external coil and implant coil (as coupled to each other based on a given separation distance and load) in the oscillator circuit that sets the frequency of the signal that is coupled between the external coil and implant coil. Such circuit is somewhat self-compensating because as the transfer efficiency starts to go down (e.g., because the separation distance changes, or because the load changes) the frequency of the signal used to couple energy into the implant coil automatically changes in a direction that tends to retune the coupled coils so that the energy transfer becomes more efficient.

Disadvantageously, changing the frequency of the signal coupled into the implant circuit may also create regulatory problems. That is, regulatory agencies may be very strict about the frequencies of signals that are allowed to be transmitted, even if only transmitted over short distances.

In view of the above, it is evident that what is needed is a transmission scheme for use with a medical implant device that optimally transfers power to the implant device from an external device at a fixed frequency, i.e., that transfers power into the implant device from the external device with minimum power loss. The present invention addresses this and other needs.

SUMMARY OF THE INVENTION

The present invention addresses the above and other needs by providing a directional coupler and an impedance matching circuit in the external device. The directional coupler allows the forward power being transferred to the implant device, as well as the reverse power being reflected form the implant device (as a result of an impedance mismatch) to be sensed and monitored. At optimum power transfer conditions, i.e., when this is an impedance match between the external device and the implant device, the forward power is a constant and the reverse power is zero.

The impedance matching circuit that forms part of the invention allows the impedance of the external circuit to be selectively adjusted, e.g., by changing component values, so that it matches the impedance of the implant circuit for a given coil separation distance and a given load. In accordance with one aspect of the invention, at least one electronically-adjustable component is used within the impedance matching circuit within the external device whose value is automatically adjusted by the reverse power sensed through the directional coupler. In this way, while operating at a fixed frequency, the impedance of the impedance matching circuit in the external device is automatically altered, as needed, in order to force the sensed reverse power to a minimum value, e.g., zero, thereby providing a matched impedance condition which assures optimum power transfer between the external device and the implant device.

In accordance with another aspect of the invention, the directional coupler utilized within the external device provides a reverse power signal indicative of the impedance mismatch that exists at any given time between the external device and implant device. Such reverse power signal is then used as a feedback signal that controls adjustments made to the impedance of the external impedance matching circuit so that the impedance of the external device automatically changes to match the impedance of the implant device.

In accordance with yet an additional aspect of the invention, the impedance matching circuit utilized within the external device includes at least one varactor diode, which varactor diode provides a capacitance value that varies as a function of an applied back-bias control voltage. The control voltage, in turn, is derived from the reverse power signal obtained from the directional coupler.

It is a feature of the invention to provide an automatically adjustable impedance matching circuit for use within the external device of an implantable medical system, such as an implantable cochlear stimulation (ICS) system, that is able to maintain an optimum power transfer between the external device and implant device despite variations in separation distance and/or implant load.

It is another feature of the invention to provide an automatically adjustable impedance matching circuit for use within an external device that is capable of automatically matching its output impedance to the impedance of the implant device despite variations in the separation distance and/or implant load that may vary by as much as a factor of ten.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
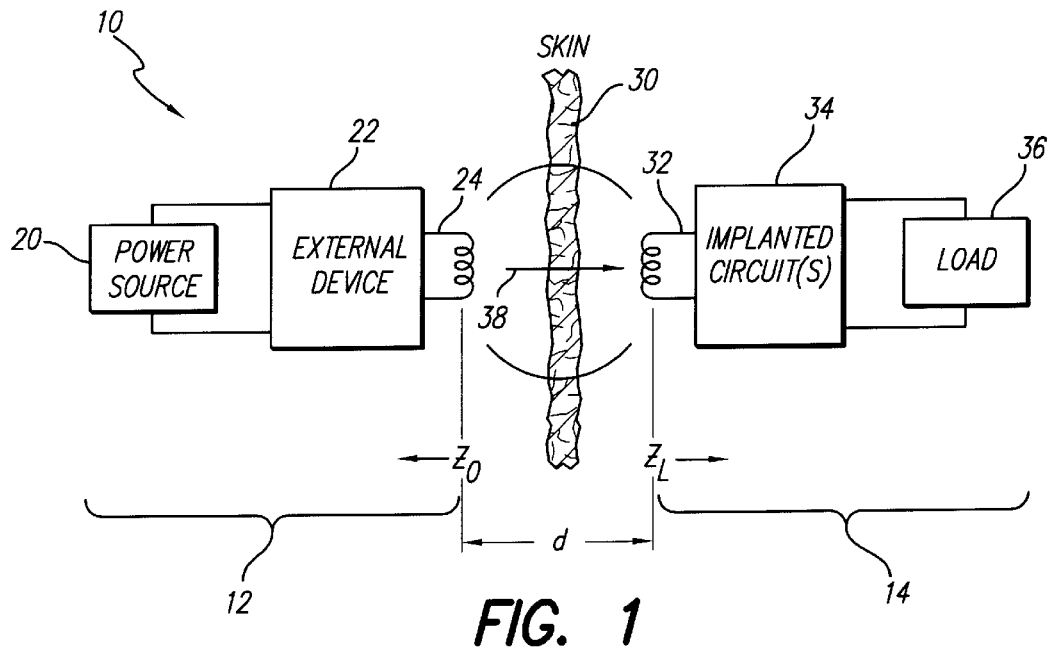
FIG. 1 is block diagram illustrating the use of an external device to inductively couple power into an implant device.

Turning first to FIG. 1, there is shown a block diagram of a power transfer system 10 that includes an external power transfer system 12 and an implanted device 14. The external power transfer system 12, also referred to as the external system 12, includes a power source 20, an external device or circuit 22, and an external coil 24. As used herein, the word "external" means not-implanted, e.g., on the outside of the skin 30, of a patient or user.

The implanted device 14, as seen in FIG. 1, includes an implanted coil 32, an implanted circuit(s) 34, and a load 36. As used herein, the term "implanted" means implantable subcutaneously, i.e., placed under the skin 30 of the user or patient. For some embodiments of the invention, it is contemplated that the power transfer system 12 may itself be implanted, wholly or partially, the invention for such embodiment thus being directed to the transmission of power between two implantable devices.

For purposes of the present invention, the function performed by the implanted or implantable device 14 is not important. The implant device 14 may perform any desired function, e.g., tissue stimulation, sensing and monitoring physiological parameters, injecting medication into the blood or tissue of the patient, and the like. A preferred application for the invention is for use with an implantable cochlear stimulator (ICS), which ICS provides stimulation to the auditory nerve fibers in the cochlea of the patient as a function of sounds sensed external to the patient. A representative ICS system is illustrate in U.S. Pat. No. 5,603,726. incorporated herein by reference.

Regardless of the type of function performed by the implant device 14, it must receive operating power from the external system 12. Typically, power is transferred into the implant device 14 via inductive coupling. That is, an ac power signal, generated by the external device 12 is applied to the external coil 24. This ac power signal induces a corresponding ac power signal in the implanted coil 32 whenever the external coil 24 and the implant coil 32 are sufficiently close to each other so as to permit the alternating magnetic field created by passage of the ac power signal in the external coil 24 to pass through the implanted coil 32. Such magnetic coupling of two coils is commonly referred to as inductive coupling.

The power coupled from the external coil 24 to the implanted coil 32 is represented in FIG. 1 by the straight arrow 38. The magnitude of the coupled power 38 is predominately a function of the distance between the two coils 24 and 32 as well as the impedance match between the implant device 14 and the external device 12.

The distance between the two coils 24 and 32 is referred to herein as the "implant distance", and is represented in FIG. 1 as the distance "d".

The input impedance of the implanted device 14 is represented in FIG. 1 by the symbol $Z_L$. The value of $Z_L$ is determined in large part by the value of the load 36 attached to the implanted device 34, as well as the components used to make the implanted circuit(s) 34. The value of the load 36 varies significantly from patient to patient, and over time for the same patient. Thus, the input impedance $Z_L$ of the implant device 14 is not a constant, as has often been assumed in the past, but is a variable that may vary over time and from patient to patient by as much as a factor of 10 or more.

The output impedance of the external system 12 is represented in FIG. 1 by the symbol $Z_0$. The value of $Z_0$ is determined in large part by the circuit components from which the external device 22 is made.

It is an object of the present invention to provide an external system 12 for coupling power into an implant device 14 that automatically adjusts the output impedance $Z_0$ of the external system to match the input impedance $Z_L$ of the implant device 14. When such an impedance match is achieved, i.e., when $Z_0 \approx Z_L$, then an optimum power transfer condition exists, and a maximum amount of power 38 may be coupled into the implant device.

Figure 2:
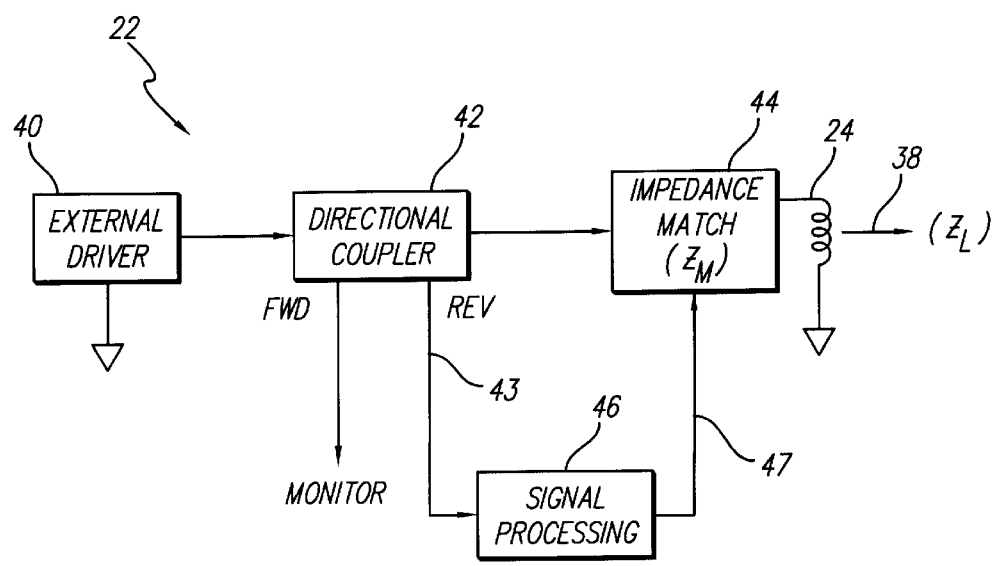
FIG. 2 is a functional block diagram of an external power transfer system made in accordance with the present invention, which external power transfer system includes a directional coupler and an impedance matching circuit.

In order to achieve the above objective, the present invention includes circuitry within the external device 22 as shown in the block diagram of FIG. 2. As seen in FIG. 2, the external device 22 includes an external driver circuit 40 which generates the ac power signal, preferably a fixed frequency ac power signal. By way of example, in an ICS type of system, the ac power signal may comprise a 49 MHz signal. This ac power signal is coupled through a directional coupler 42 and an impedance match circuit 44. The directional coupler, as is known in the art, senses both the forward power passing through the directional coupler towards the external coil 24, and the reverse power reflected back from the coil 24 as a result of impedance mismatch.

Figure 3A:
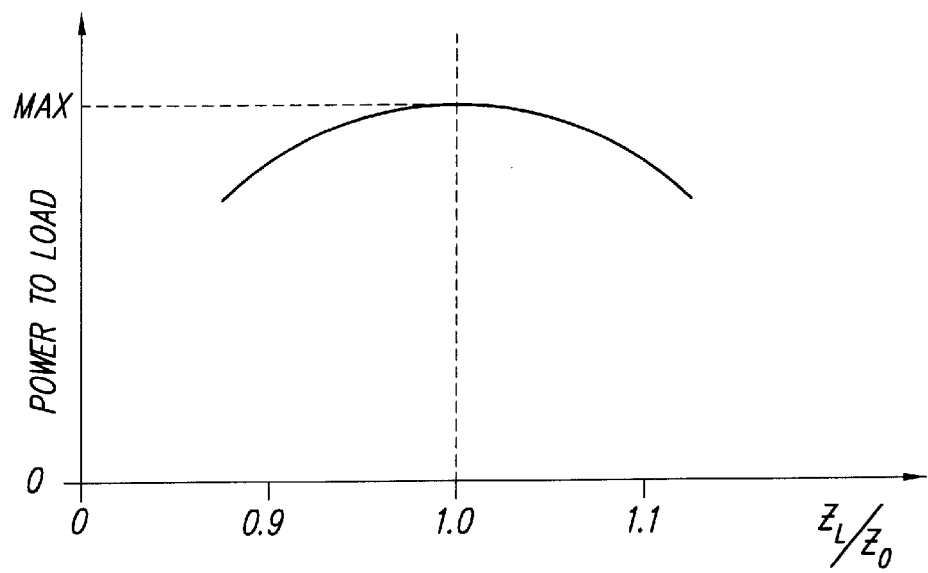
FIG. 3A is a graph that qualitatively illustrates how the amount of power delivered to the implantable device varies as a function of the impedance match between the output impedance $Z_0$ of the external system and the input impedance $Z_L$ of the implantable device.
Figure 3B:
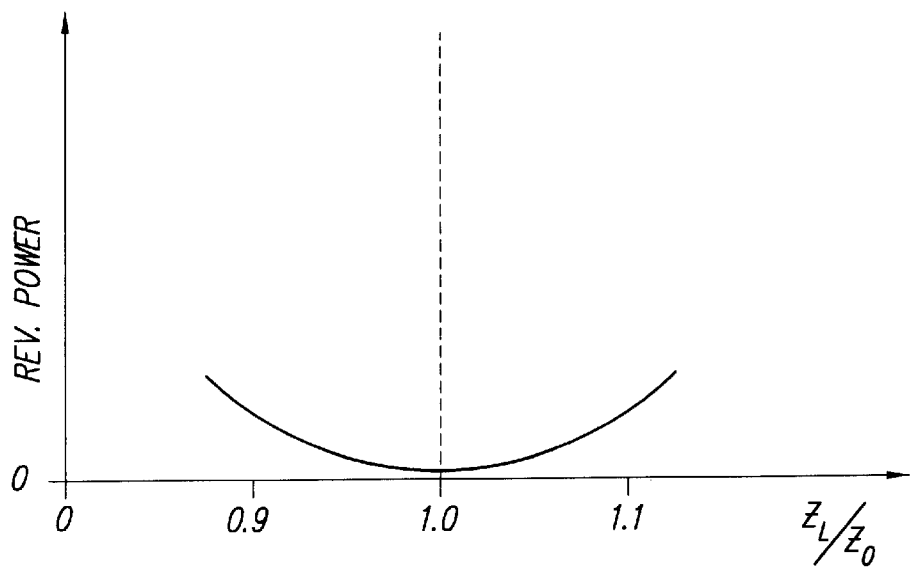
FIG. 3B is a graph that qualitatively illustrates how the reverse power sensed by the directional coupler varies as a function of the impedance match between the output impedance $Z_0$ of the external system and the input impedance $Z_L$ of the implantable device.

To explain forward power and reverse power in more detail, reference is momentarily made to FIGS. 3A and 3B, which qualitatively illustrate the power delivered to a load (FIG. 3A) and the reverse power reflected from a load (FIG. 3B) as a function of the impedance match between the impedance of the circuit delivering the power ($Z_0$) and the impedance of the circuit receiving the power ($Z_L$). As seen in FIG. 3A, a maximum amount of power is delivered to the receiving circuit (i.e., to the load) when the output impedance $Z_0$ of the circuit delivering the power matches the input impedance $Z_L$ of the circuit receiving the power, i.e., when the ratio of $Z_L/Z_0$ is approximately equal to 1.0. If an impedance mismatch exists, i.e., if the ratio of $Z_L/Z_0$ is not equal to 1.0, then much of the power directed to the receiving circuit is reflected back to the delivering circuit rather than being transferred to the receiving circuit. Thus, as qualitatively shown in FIG. 3B, the reverse power, or power reflected away from the receiving circuit, is at a minimum, e.g., is approximately zero, when an impedance match exists. However, when an impedance mismatch exists, i.e., when the ratio of $Z_L/Z_0$ is not equal to 1.0, then the reverse power increases. The more the mismatch, the higher the magnitude of the reverse power.

The present invention uses the sensed reverse power as a control signal to indicate when an impedance mismatch exists, and hence when a less-than-optimum power transfer condition exists. That is, as seen in FIG. 2, the directional coupler 42 provides a reverse power terminal or signal line 43 on which a signal representative of the sensed reverse power appears. This signal is directed to a signal processing circuit 46. The signal processing circuit 46, in turn, converts the sensed reverse power signal to a control signal, appearing on signal line 47, which is directed to the impedance matching circuit 44. The impedance matching circuit 44 responds to the control signal on signal line 47 by changing the value of its impedance in a direction that moves it closer to the input impedance $Z_L$ of the implant device 14. This feedback action thus drives the sensed reverse power to a minimum value, e.g., zero, at which point an impedance match condition exists, and power is optimally transferred to the implant device 14.

It is thus seen that the present invention, by sensing the reverse power through the use of the directional coupler 42, provides a type of negative feedback system that automatically alters the impedance of the impedance matching circuit 44 so that it matches the input impedance $Z_L$ of the implant device 12. Thus, without changing the frequency of the ac power signal, generated by the external driver circuit 40, optimum power transfer conditions may be maintained, thereby making the transfer of power into the implant device more efficient, i.e., with less loss.

It is to be emphasized that the block diagram of the external device 22 as shown in FIG. 2 is functional. Those of skill in the art should readily be able to fashion numerous types of circuits that carry out the functions illustrated in FIG. 2. In doing so, both analog and digital circuitry may be employed. That is, although not illustrated specifically in FIG. 2, it is to be understood that while the ac power signal generated by the external driver circuit 40 will comprise an analog signal, the sensed reverse power signal may be converted to a digital signal, and the signal processing performed within the signal processing circuit 46 may thus be carried out digitally, e.g., using a microprocessor or other suitable digital signal processor (DSP) circuit. Then, as needed, the control signal(s) generated by the DSP (there may be more than one control signal) or other processing circuit 46, may be converted back to an analog signal for use by the impedance matching circuit. Some portions of the impedance matching circuit may also be implemented digitally, e.g., through the use of DSP circuits that carry out the functions of digital filter circuits, and the like.

Figure 4:
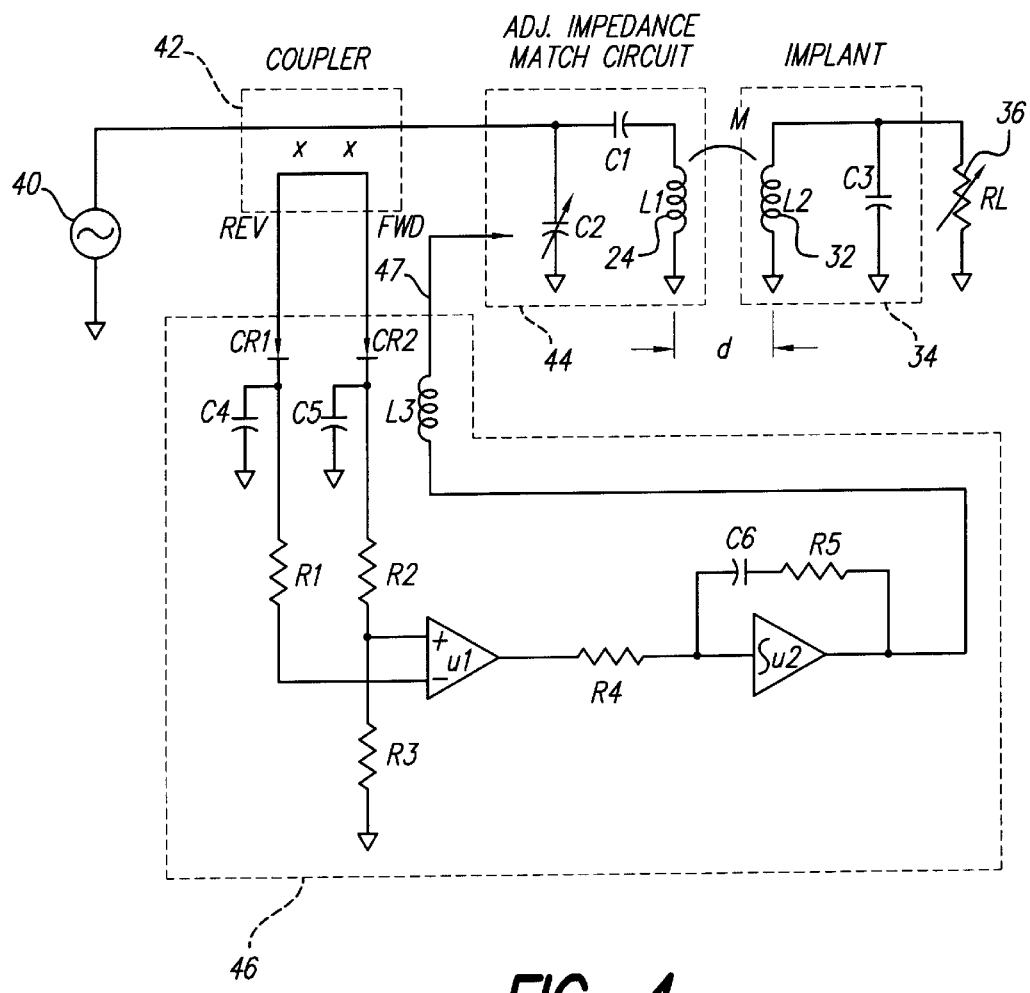
FIG. 4 shows a schematic diagram of an analog embodiment of the present invention.

Turning next to FIG. 4, there is illustrated an exemplary analog embodiment of the present invention. As seen in FIG. 4, an driver circuit 40, which is of conventional design, generates an ac power signal. this ac power signal is coupled through directional coupler 42 and impedance matching circuit 44 to external coil 24, which coil 24 actually forms part of the impedance matching circuit 44. The external coil 24 is inductively coupled with an implant coil 32, which coil forms part of the implant device 34.

Directional coupler 42 may be of conventional design, and in fact for an ac signal in the 49 MHz range, may be a commercially-available directional coupler, such as part number PDC-20-1 available form Mini-Circuits of Brooklyn, N.Y.. Numerous other commercially-available directional couplers, available from other manufacturers, may also be used.

The signal processing circuit 46, for the exemplary embodiment shown in FIG. 4, may comprises a simple half rectifier circuit comprising diode CR1 and capacitor C4 for converting the sensed reverse power signal to a dc voltage level. Similarly, another half rectifier circuit, comprising diode CR2 and capacitor C5, converts the sensed forward power signal to a dc voltage level. The dc voltage levels representing the sensed reverse power is applied to the "−" terminal of a high gain operational amplifier U1 through resistor R1. The "+" terminal of the amplifier U1 is connected to the common node of series-connected resistors R2 and R3, which resistors form a voltage dividing network. As seen in FIG. 4, the other node of resistor R2 is connected to the dc voltage level representing the sensed forward power (i.e., is connected to capacitor C5), and the other node of resistor R3 is connected to ground. Thus, the signal appearing at the "+" terminal of amplifier U1 comprises a reference voltage that is derived from the forward power signal. The output of amplifier U1 is connected to an integration circuit, made up of operational amplifier U2, resistors R4 and R5, and capacitor C6. The design of such integration circuits is conventional.

The output of the integration circuit U2 is coupled as a control signal through inductor L3 to variable capacitor C2. Variable capacitor C2 assumes a capacitance value as a function of this control signal. In a preferred embodiment, the variable capacitor C2 is realized using an electronic variable capacitor, e.g., a varactor diode capacitor, included within the impedance matching circuit 44. Also included within the impedance matching circuit 44 is a coupling capacitor C1 and the external coil 24, which has an inductance L1. These elements are connected in a π configuration, with the variable capacitor C2, e.g., varactor diode capacitor C2, and the coil L1 forming the legs of the π circuit, and the coupling capacitor C1 forming the top bridge of the π circuit.

It should be emphasized that the impedance matching circuit 44 illustrated in FIG. 4 is a very simple impedance matching circuit that includes only three elements, varactor (variable capacitor) C2, fixed capacitor C1, and L1. Other, more complex, impedance matching circuits may be utilized, as needed or desired.

The output impedance $Z_0$ of the impedance matching circuit 44 is a function of the values of the components that make up the circuit. That is, the value of $Z_0$ is determined by the values of L1, C1 and C2. Because C2 is variable, determined as a function of the voltage applied across it, the output impedance $Z_0$ is thus also variable.

In operation, the driver circuit 40 generates an ac power signal that is coupled to the external coil 24 through the directional coupler 42 and the impedance matching circuit 44. If an impedance mismatch is present, then there will be some reverse power sensed by the directional coupler. There will also, of course, be some forward power sensed by the directional coupler. The sensed reverse power drives the output of amplifier U1 in a direction that causes the voltage applied to the varactor C2, as integrated by the integration circuit U2, to change the value of C2 so that the value of the output impedance $Z_0$ moves in a direction to match the input impedance $Z_L$. This action, in turn, forces the reverse power to a minimum value, e.g., zero. Advantageously, the gain of the amplifier circuit U1 and integration circuit U2 is such that the output impedance $Z_0$ varies as required to maintain the reverse power at or near zero, thus assuring an optimum impedance match between the external device and implant device, despite variations that may occur in the implant distance and load of the implant device.

For a typical ICS application, the implant distance may vary from near 0, e.g., 1–3 mm, to about 15 mm, while the load may vary from between about 20 Ω to about 300 Ω. It is thus seen that both the load and implant distance may vary by more than a factor of 10. This means, if the output impedance of the external device 14 is also to vary by a corresponding amount, the value of the variable capacitor C2 must also vary by a similar amount.

Tests conducted have shown that for an ac power signal operating at about 49 MHz, and for an implant range of 3–12 mm, and a load that varies from 20–300 Ω, a varactor diode (variable capacitor) that ranges between about 10–100 pf allows the output impedance $Z_0$ to remain matched to the input impedance $Z_L$, despite wide fluctuations in $Z_L$ occasioned by variations in the implant distance and load as indicated above.

It is thus seen that the present invention provides an automatically adjustable impedance matching circuit for use within an external device of an implantable medical system, such as an implantable cochlear stimulation (ICS) system, wherein an optimum power transfer condition is maintained between the external device and implant device despite variations in separation distance and/or implant load.

It is further seen that the invention provides an automatically adjustable impedance matching circuit for use within an external power transfer device that is capable of automatically matching its output impedance $Z_0$ to the input impedance $Z_L$ of the implant device despite variations in the separation distance and/or implant load that may vary by as much as a factor of ten.

While the invention herein disclosed has been described by means of specific embodiments and applications thereof, numerous modifications and variations could be made thereto by those skilled in the art without departing from the scope of the invention set forth in the claims.

What is claimed is:

1. An external power coupling system for optimally coupling power to an implantable device at a fixed frequency, the implantable device having an input impedance that varies as a function of implant distance and implant load, the power coupling system comprising:

eternal driver means for generating an ac power signal at a fixed frequency;

an external coil for receiving the ac power signal and inductively coupling the ac power signal to the implantable device;

an impedance matching circuit interposed between the external coil and external driver means for setting an output impedance of the power coupling system, the impedance matching circuit having means for adjusting the output impedance as a function of a control signal;

directional coupler means coupled to the ac power signal for sensing reverse power;

signal processing means for generating the control signal as a function of the sensed reverse power, and applying the control signal to the impedance matching circuit so as to adjust the output impedance to match the input impedance of the implantable device.

2. The external power coupling system of claim 1 wherein the signal processing means comprises means for generating the control signal so that it causes the output impedance to increase to match an increase in the input impedance of the implantable device, and to decrease to match a decrease in the input impedance of the implantable device.

3. The external power coupling system of claim 1 wherein the impedance matching circuit includes at least one varactor that functions as a variable capacitor having a capacitance that varies as a function of a voltage applied thereto, the varactor comprising the means by which the output impedance of the power coupling system is adjusted.

4. The external power coupling system of claim 1 wherein the directional coupler means comprises a directional coupler circuit providing a forward power signal and a reverse power signal, and wherein the directional coupler circuit is interposed intermediate the external driver means and the impedance matching circuit.

5. The external power coupling system of claim 4 wherein the signal processing means comprises an analog circuit having means for comparing the forward power signal to the reverse power signal and generating a difference signal as a function of the difference therebetween, and means for integrating the difference signal to produce the control signal.

6. The external power coupling system of claim 4 wherein the signal processing means comprises a digital circuit having means for digitizing the reverse power signal to produce a digitized reverse power signal, digital signal processing (DSP) means for processing the digital reverse power signal in accordance with a prescribed processing program to produce a digitized control signal, and means for converting the digitized control signal to an analog control signal for application to the impedance matching circuit.

7. A power coupling circuit for optimally coupling power to an implantable stimulation device, the implantable stimulation device having an input impedance that varies as a function of implant distance and implant load, the power coupling circuit comprising
   a transmission coil;
   a driver circuit that generates an ac power signal, the ac power signal being applied to the transmission coil, where it is inductively coupled to the implantable stimulation device; and
   an adjustable impedance matching system that automatically matches the impedance of the power coupling circuit to match the input impedance of the implant device.

8. The power coupling system of claim 7 wherein the adjustable impedance matching system comprises:
   a sensor that senses variations in power directed to the transmission coil;
   an impedance matching circuit interposed between the transmission coil and sensor, the impedance matching circuit having an output impedance;
   means for adjusting the output impedance of the impedance matching circuit as a function of the sensed variations in the power directed to the transmission coil to match the output impedance to the input impedance of the implant device.

9. The power coupling system of claim 8 wherein the sensor senses reverse power reflected from the transmission coil, and wherein the means for adjusting the output impedance adjusts the output impedance until the sensed reverse power is reduced to a minimum value.

10. The power coupling system of claim 7 wherein the implantable stimulation device comprises an implantable cochlear stimulator (ICS), and wherein the power coupling circuit is included within an external headpiece used with the ICS.

11. The power coupling system of claim 7 wherein the means for adjusting the output impedance comprises an impedance matching circuit that includes at least one varactor diode that functions as a variable capacitor having a capacitance that varies as a function of a voltage applied thereto.

12. A method of optimally coupling power to an implantable stimulation device, the implantable stimulation device having an impedance that varies as a function of implant distance and implant load, the method comprising:
   (a) generating an external ac power signal;
   (b) applying the external ac power signal to an external transmission coil through an impedance matching circuit;
   (c) inductively coupling the external transmission coil with an implanted coil included within the implantable stimulation device;
   (d) sensing reverse power from the external transmission coil;
   (e) adjusting the impedance of the impedance matching circuit in a direction that causes the sensed reverse power to go to a minimum value;
   (f) coupling power into the implanted device while maintaining the impedance of the impedance matching circuit at that value which keeps the sensed reverse power at the minimum value of step (e).

13. The method of claim 12 wherein step (a) comprises generating an external ac power signal having a fixed frequency.

14. The method of claim 13 wherein step (a) comprises generating an external ac power signal having a fixed frequency of about 49 MHz.

15. The method of claim 13 wherein the impedance matching circuit includes a varactor element that provides a variable capacitance as a function of a voltage applied thereo, and wherein step (e) comprises adjusting the voltage applied to the varactor, wherein the capacitance provided by the varactor element varies, and wherein the impedance of the impedance matching circuit varies.

* * * * *